United States Patent [19]

Lawrence

[11] Patent Number: 4,820,646

[45] Date of Patent: Apr. 11, 1989

[54] FECAL OCCULT BLOOD TEST METHOD

[75] Inventor: Paul J. Lawrence, Campbell, Calif.

[73] Assignee: Litmus Concepts, Inc., Santa Clara, Calif.

[21] Appl. No.: 174,108

[22] Filed: Mar. 28, 1988

Related U.S. Application Data

[63] Continuation of Ser. No. 869,573, Jun. 2, 1986, abandoned, which is a continuation-in-part of Ser. No. 680,357, Dec. 11, 1984, Pat. No. 4,615,982, and a continuation-in-part of Ser. No. 2,446, Dec. 10, 1985.

[51] Int. Cl.$^4$ .................. G01N 21/78; G01N 33/72
[52] U.S. Cl. ........................................ 436/66; 435/28; 436/904
[58] Field of Search .............. 422/56, 57; 436/66, 436/135, 136, 138, 904; 435/4, 28, 805

[56] References Cited

U.S. PATENT DOCUMENTS

| | | | |
|---|---|---|---|
| 3,278,394 | 10/1966 | Harvill et al. | 435/28 X |
| 3,406,015 | 10/1968 | Foster | 435/28 |
| 3,413,197 | 11/1968 | Fraser | 435/28 X |
| 3,721,607 | 3/1973 | Gruber et al. | 435/28 X |
| 4,017,261 | 4/1977 | Svoboda et al. | 436/66 X |
| 4,071,317 | 1/1978 | Lam | 422/56 |
| 4,211,845 | 7/1980 | Genshaw et al. | 436/904 X |
| 4,318,984 | 3/1982 | Magers et al. | 435/28 X |
| 4,578,358 | 3/1986 | Oksman et al. | 436/66 |

Primary Examiner—Michael S. Marcus
Assistant Examiner—Robert J. Hill, Jr.
Attorney, Agent, or Firm—Dianne E. Reed

[57] ABSTRACT

Fecal occult blood tests of enhanced sensitivity, specificity, and readability are provided by employing (1) a developer or complete reagent solution that uses as a solvent system a solvent comprising at least about 50% by volume of a solvent for iron protoporphyrins such as dimethyl sulfoxide and/or (2) a multi-chromogen comprised of a mixture of guaiac and ABTS. Test results may be further improved by incorporating hemoprotein solubilizing agents, plant peroxidase inhibitors, iron-/copper chelating agents, accelerators and buffers in the developer/reagent.

2 Claims, No Drawings

FECAL OCCULT BLOOD TEST METHOD

CROSS-REFERENCE TO RELATED APPLICATIONS

This application is a continuation of application Ser. No. 869,573, filed June 2, 1986, now abandoned, which in turn is a continuation-in-part of application Ser. No. 680,357, filed Dec. 11, 1985, now U.S. Pat. No. 4,615,982, and PCT Application No. PCT/US85/02446, filed Dec. 10, 1985 (application Ser. No. 899,300, filed Aug. 11, 1986, now abandoned).

TECHNICAL FIELD

This invention is in the field of fecal occult blood tests (FOBT). More particularly it relates to improved FOBT that provide a reduced incidence of false results and/or greater sensitivity and specificity and/or are easier to perform.

BACKGROUND ART

FOBT are commonly used clinically to detect occult blood loss from gastrointestinal (GI) lesions. For example, carcinoma of the colon and rectum is the most serious cancer in the U.S. and second only to lung cancer in causing death—approximately 100,000 new cases and 50,000 deaths annually. Because colorectal cancer is slowly progressive with a long asymptomatic period, it provides an ideal opportunity for early detection and successful therapy. Thus, FOBT are a rational attempt at early diagnosis because the colorectal lesions frequently bleed, and routine noninvasive testing is possible. Similarly, hospitals and physicians very often utilize FOBT to detect or monitor GI lesions resulting from disease, injury, surgery, and other causes.

Early FOBT involved shipping entire 24-48 hour fecal collections in paint cans to central laboratories for testing with an acidified guaiac solution and hydrogen peroxide. Guaiac is a complex plant extract containing the leuco dye, alpha guaiaconic acid. Leuco dyes are oxidized by hydroperoxides in the presence of catalyst to form a blue color:

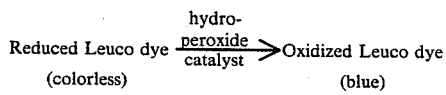

Because hemoglobin is an efficient catalyst (pseudoperoxidase), feces may be tested for occult blood using a leuco dye/hydroperoxide reagent. Nonetheless, the procedure remained very poorly utilized because of the disagreeable nature of the test and physicians were largely denied this very useful information.

U.S. Pat. No. 3,996,006 describes a FOBT technique that popularized the guaiac-based test for occult blood in feces. It employs a slide having a sheet of guaiac-impregnated paper between a front panel and a rear panel with openings in the panels and pivotal flaps to cover the openings. A fecal specimen is placed on the paper through the opening in the front panel and that panel is closed. The rear panel is then opened and a hydrogen peroxide developer is placed on the paper via the opening in the rear panel. If blood is present in the specimen, the paper will turn blue. A commercial embodiment of this test, called the HEMOCCULT ® test, is widely used in the hospitals and physicians' offices. Despite the widespread popularity of the HEMOCCULT ® test, recent studies have pointed out serious limitations in its sensitivity and specificity. Applicant believes that the sensitivity limitation is due partly to (1) the fact that hemoglobin in many specimens is degraded to derivatives that exhibit little or not peroxidative activity, (2) degradation of peroxidatively active hemoproteins by the hydroperoxide reagent used in the test and (3) the relative insolubility of the degraded products (i.e., iron protoporphyrins such as heme and hemin) in the reagents used in the test. Sensitivity limitations, of course, may cause false negative results. The specificity limitation is probably due to the response of the test to plant peroxidases and/or iron or copper in the specimens or the environment in which the test is run. Specificity limitations lead to false positive results.

U.S. Pat. No. 4,333,734 decribes a variation in the guaiac-based FOBT that is intended to reduce the incidence of false positive results due to the presence of plant peroxidases in the specimen. It includes a peroxidase denaturing agent such as urea or guanidine hydrochloride together with a metal chelating agent to sequester calcium and magnesium ions that are essential to peroxidase activity. The denaturant and the chelating agent are formulated with the guaiac.

U.S. Pat. No. 4,071,317 relates to using polar solvents such as dimethyl sulfoxide (DMSO) and dimethyl formamide (DMF) to stabilize mixtures of organic hydroperoxides and leuco dyes that are used in FOBT. The solvent is formulated in minor proportions with the hydroperoxide and leuco dye. This solution is applied to a solid matrix and the matrix is dried prior to use in testing.

Several references indicate that monomeric species of iron protoporphyrins exhibit greater peroxidase activity than dimeric or aggregated species. *Biochem J* (1970) 117: 741–744; *Biochem J* (1973) 135: 353–359; *Biochem J* (1976) 153: 279–285; and *Biochemistry* (1974) 13: 4279–4284. *Biochem J* (1979) 179: 281–289 indicates that hemin occurs in its monomeric form in mixtures of DMSO and water that contain in excess of about 35% (v/v) DMSO.

*Biochem J* (1968) 108: 131–136 discusses the solubility of nitrogenous ligand-alkaline hematin complexes. *Biochimica et Biophysica Acta* (1977) 498: 205–214 describes the use of various water-soluble polymers such as polyethylene oxide, polyvinyl alcohol, polyvinyl pyrrolidone, and polystyrene sulfonate to dissolve aggregates of ferroheme and protoporphyrin in alkaline aqueous media.

An object of the present invention is to reduce the incidence of incorrect results (both false positive and false negative) in leuco dye-based FOBT. This is achieved by applying the hydroperoxide or both the hydroperoxide and leuco dye to the specimen in a solution that uses a solvent system that dissolves iron protoporphyrins. Another object is to provide a chromogen that improves test readability and a complete FOBT reagent containing that chromogen.

DISCLOSURE OF THE INVENTION

One aspect of the invention is a chromogen for use in a test for perioxidative activity, such as an FOBT, comprising a mixture of guaiac and 2,2'-azino-di-(3-ethylbenzyl) thiazoline sulfonic acid (ABTS).

Another aspect of the invention is an improvement in a fecal occult blood test method comprising contacting a fecal specimen on a solid test matrix with a leuco dye and a hydroperoxide, the improvement being that the hydroperoxide or the hydroperoxide and the leuco dye are applied to the fecal specimen in solution in a solvent comprising at least 50% by volume of a solvent for iron protoporphyrins whereby the iron protoporphyrins in the specimen are dissolved.

Still another aspect of the invention is a fecal occult blood test method comprising contacting a fecal specimen on a solid test matrix with a leuco dye and a hydroperoxide wherein the leuco dye comprises a mixture of guaiac and ABTS.

Still another aspect of the invention is an FOBT reagent comprising a hydroperoxide or a hydroperoxide and a leuco dye in solution in a solvent for iron protoporphyrins selected from the group consisting of:

(a) pyridine;

(b) a mixture of ethanolamine and a co-solvent selected from the group consisting of methyl ethyl ketone, tetramethylene sulfone, butyrolactone, glycerol, methanol, tetrahydrofurfuryl alcohol, 2-methoxy ethanol, and tetramethyl urea;

(c) a mixture of 2-(diethylamino)ethylamine and a co-solvent selected from the group consisting of methyl ethyl ketone, acetonitrile, tetramethylene sulfone, butyrolactone, tetrahydrofurfuryl alcohol, 2-methoxy ethanol, and methanol;

(d) a mixture of diethanolamine and a co-solvent selected from the group consisting of methyl ethyl ketone, acetonitrile, tetramethylene sulfone, butyrolactone, and tetrathydrofurfuryl alcohol; and (e) 1-methyl-2-pyrrolidinone.

MODES FOR CARRYING OUT THE INVENTION

As used herein the term "hemoprotein" is intended to include hemoglobin and derivatives of hemoglobin such as heme and hemin that have the ability (particularly in their monomeric form) to catalyze the transfer of oxygen from a hydroperoxide to a leuco dye to cause the leuco dye to be oxidized and thereby produce a detectable response. Such ability is sometimes referred to herein as "peroxidative activity".

As used herein the term "leuco dye" is not intended to be limited to a particular chemical species or genus but is intended to encompass indicators that produce a detectable response, typically a color change that is visible to the naked eye, when oxidized in the presence of a hemoprotein. Examples of leuco dyes are guaiac, benzidine, o-tolidine, cresol, catechol, 3,3',5,5'-tetramethylbenzidine, p-tolidine, betanaphthol, pyrogallol, o-phenylenediamine, leuco malachite green, 3-amino ethylcarbazole, 4-amino antipyrine, phenol, and ABTS.

The various aspects of the invention may be employed separately or combined to improve FOBT. As indicated one aspect is the use of a mixture of guaiac and ABTS as a chromogen in FOBT. Another is applying to the fecal specimen a developer or complete reagent solution that uses as its solvent system a solvent for iron protoporphyrins.

The chromogen mixture of the invention may be used in various FOBT formats that involve contacting a fecal specimen placed on a solid test matrix with a leuco dye and a hydroperoxide. In one format the matrix is impregnated with the mixture (i.e., the matrix carries the mixture in dry form) beforehand. In another the matrix is impregnated with one of the components of the mixture and the other is applied in solution to the matrix/specimen either combined with or separately from the hydroperoxide. For long-term stability, it is preferred to keep the chromogen mixture and hydroperoxide separate. For instance, they might be packaged in separate containers adapted for simultaneous dispensing, such as a double-barreled syringe with a common outlet nozzle. Another format is to employ the chromogen in solution as part of a complete reagent (when long-term stability is not involved). The complete reagent contains, in addition to the mixture and the solvent, a hydroperoxide and, optionally, other additives such as hemoprotein solubilizing agents, stabilizers, vegetable peroxidase inhibitors, iron chelators, accelerators, and buffers. Such additives may, of course, be impregnated into the solid test matrix in the other test formats. Use of a complete reagent has the advantages of avoiding the need to impregnate the matrix beforehand, permitting new test geometries, lower manufacturing costs and use of untreated matrixes, and improving test performance.

In addition to use in FOBT, the chromogen mixture may be used advantageously in other common colorimetric tests for the presence of peroxidatively active molecules other than hemoproteins.

The chromogen mixture of guaiac and ABTS produces a color response that is greater than the sum of the responses that would be expected from the individual components. In addition to enhanced color intensity, the color is spread more evenly than the observed in current (e.g., HEMOCCULT ® test) FOBT, is more stable (i.e., long-lasting), and is more reproducible. The weight ratio of guaiac to ABTS in the mixture will be in the range of 1:5 to 5:1, preferably approximately 1:1. When the chromogen mixture is formulated as a complete reagent with a peroxide and/or in a solvent for iron protoporphyrins such as DMSO, it is preferable to include a stabilizing amount of sodium sulfite or other antioxidant in the formulation. Preferably the sodium sulfite is present in amounts in excess of that which saturates the solution. The concentration of the chromogen mixture in the solution will usually be in the range of 0.5 to 10% by weight.

Similarly, the application to the fecal specimen of a developer/complete reagent having a solvent system based on a solvent for iron protoporphyrins may be used in a variety of FOBT formats. When used as a developer, the solution will contain the hydropreroxide and be applied to the specimen on a leuco dye-impregnated matrix. When used in the form of a complete reagent, the solution will contain a leuco dye, preferably the multi-chromogen of the invention, together with the hydroperoxide and, optionally, other additives such as those described above.

The test matrixes used in the FOBT methods of the invention may be made from a variety of porous materials such as cellulosics (wood, paper), ceramic, glass fibers, natural or synthetic cloth fibers, felt, and sponge. Bibulous filter paper is commonly used and is preferred.

The liquids that are useful a solvents for iron protoporphyrins should preferably have an intermediate to high capacity to dissolve iron protoporphyrins at a pH in the range of about 6.5 to 7.5. In the present instance such capacity was determined by mixing 25 mg crystalline hemin with 1 ml of solvent at ambient temperature, and measuring the amount of hemin remaining undissolved. Liquids evaluated by this procedure that exhibited a high capacity for dissolving hemin included aprotic amides, sulfoxides, sulfones, pyridine and mixtures of certain amines and other organic solvents.

The amides that were found to be acceptable iron protoporphyrin solvents are of the formula

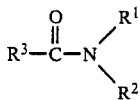

wherein $R^1$, $R^2$, and $R^3$ are the same or different and represent hydrogen, lower alkyl, phenyl or benzyl, with the provisions that both of $R^1$ and $R^2$ are not hydrogen and $R^3$ may be linked with $R^1$ and $R^2$ to form a 5- or 6-membered heterocycle. The term "lower" as used to modify "alkyl" denotes moieties of 1 to 6 carbon atoms. Examples of such moieties are methyl, ethyl, isopropyl, butyl, and hexyl. Dimethyl formamide and 1-methyl-2-pyrrolidinone are preferred solvents of this class.

Sulfoxides and sulfones that were found to be acceptable iron protoporphyrin solvents are of the formula

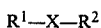

wherein X is

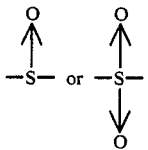

and $R^1$ and $R^2$ are the same or different and are lower alkyl, phenyl, benzyl, or, when X is

$R^1$ and $R^2$ may be linked to form a 5 or 6 membered heterocycle (e.g., tetramethylene sulfoxide, pentamethylene sulfoxide).

The mixtures of neutralized amines and organic solvents that were found to be accpetable iron protoporphyrin solvents include: ethanolamine with glycerol, tetrahydrofurfuryl alcohol, 2-methoxy ethanol, methyl ethyl ketone, tetramethyl urea, sulfolane (tetramethylene sulfone), or butyrolactone; 2-(diethylamino)ethylamine with methyl ethyl ketone, acetonitrile, sulfolane, butryolactone, tetrafurfuryl alcohol, 2-methoxy ethanol, or methanol and diethanolamine with methyl ethyl ketone, acetonitrile, sulfolane, butyrolactone, or tetrahydrofurfuryl alcohol. Other mixtures of neutralized amines and organic solvents that are suitable solvents for iron protoporphyrin may be determined empirically as described herein. The mixtures are preferably mixed at volume ratios of 1:1 based on 1M aqueous neutralized amine.

The iron protoporphyrin solvent is also preferably one that wets the test matrix so that it is capable of transporting (chromatographing) dissolved iron protoporphyrin away from the specimen so that the color change, if any, is more easily seen and not obscured by the specimen.

Cosolvents such as water, alkanols (e.g., methanol, ethanol, and other lower alkanols), pentane, ethylacetate, cyclohexane, and acetone may be included with the iron protoporphyrin solvent, but the proportion of principal solvent in the solvent compositions should be maintained above about 50% (v/v), preferably above about 75% (v/v).

Dimethylsulfoxide (DMSO) is a particularly preferred iron protoporphyrin solvent. The use of DMSO as the solvent in the developer/complete reagent provides several advantages. Firstly, it is an excellent solvent for hemoproteins, including iron protoporphyrins. Secondly, it converts heme and hemin dimers and aggregates into the monomeric forms. And, thirdly, it inactivates peroxidases that may be present in the fecal specimen and inhibits them from catalyzing the oxidation of the indicator and producing a false positive result.

Hemoprotein solubilizing agents that may be optionally included in the solution or test matrix include detergents and water-soluble polymers. Detergents that have suitable hydrophilic-hyrophobic balance to solubilize hemoproteins are suitable. Such detergents include the TRITON ® detergents (polyoxyethylene alkylphenols), detergents from the series alkyltrimethylammonium bromides, like cetyl alkyltrimethylammonium bromide (CTAB) or p-toluene sulfonic acid salts of alkyltrimethylammonium bromide detergents, and $C_{10}$ to $C_{14}$ alkali metal salts of fatty acids or alkali metal alkyl sulfates. Examples of suitable detergents are sodium dodecyl sulfate (SDS), sodium dodecyl sulfonate, sodium decyl sulfate, sodium tetradecyl sulfate, sodium tridecyl sulfonate, sodium myristate, sodium caprate, sodium dodecyl N-sarcosinate, and sodium tetradecyl N-sacrosinate. The water-soluble polymers that may be used to solubilize hemoproteins include poly(ethylene oxide), poly(vinyl alcohol), poly(vinyl pyrrolidone), poly(vinyl pyridine), and poly(styrene sulfonate). These solubilizing agents not only solubilize hemoproteins, but are believed to convert peroxidatively inactive hemoprotein dimers or aggregates into peroxidatively active monomeric species.

Nitrogenous ligands that stabilize iron protoporphyrins and enhance their peroxidative activity may also be incorporated in the complete reagent or test matrix. Examples of such ligands are pyridine, histidine, caffeine, imidazole, and imidazole derivatives.

Quinoline and quinoline derivatives may be included in the developer/complete reagent to accelerate the color formation. A preferred quinoline derivative is 7-chloro-4-(4-diethylamino-1-methyl(butylamino)-quinoline.

Other additives such as vegetable peroxidase inhibitors and iron chelators (e.g., ethylenediamine tetraacetic acid N, N, N', N'- diamino cyclohexane tetraacetic acid, citric acid, tartaric acid, nitrilotriacetic acid, diethylenetriamine-pentaacetic acid, N,N'-bishydroxyethyl glycine, ethyleneglycol bis(2-aminoethylether)-tetraacetic acid, N-hydroxyethylethylenediaminetetraacetic acid) may be incorporated into the test matrix to further reduce the likelihood of false test results. Buffers are added to maintain a suitable pH range for oxidizing the leuco dye. The particular buffer (pH range) will depend on the leuco dye that is used. The pH will usually be between about 3 and about 9. By way of example, guaiac oxidation is bufferd at pH 6-7.5 (phosphate buffer), 3,3',5,5'-tetramethylbenzidine oxidaton is buffered at a pH of about 4 (acetate buffer), and ABTS is buffered at a pH of about 9-9.5 (glycine buffer). For the chromogen mixture of the invention the pH should be in the range of 5 to 10.

Hydrogen peroxide or organic hydroperoxides such as cumene hydroperoxide, t-butyl hydroperoxide, diisopropylbenzene hydroperoxide, and 2,5-dimethylhexane hydroperoxide may be used in the developer or complete reagent. It is preferred to use an organic hydroperoxide since organic hydroperoxides are less likely to (a) produce false positive results in FOBT in which vegetable peroxidases are present in the fecal specimen and (b) destroy the peroxidase activity of the hemoprotein. The concentration of hydroperoxide in the developer/complete reagent will usually be in the range of 0.05 to 10% by volume, more usually 0.5 to 5% by volume.

The FOBT materials and procedures of the invention and their advantages over previous materials and procedures are illustrated by the following examples. These examples are not intended to limit the invention in any manner.

EXAMPLE 1

Tests were carried out to compare the specificity and sensitivity achieved in FOBT with a developer composition consisting of (5% (v/v) cumene hydroperoxide (CHP) in DMSO) versus that achieved with a conventional FOBT developer (3–6% (v/v) hydrogen peroxide in ethanol/water).

Serial dilutions of hemin (Hm, 0.1 mg/ml in 1mM ammonium hydroxide), hemoglobin (Hb, 1.0 mg/ml), and horseradish peroxidase (HRPO, 20 U/ml) in water were prepared. Two $\mu$l of these dilutions were applied to HEMOCCULT ® slides and the spots were allowed to dry. Five $\mu$l of developer composition was applied to each spot. After one minute the presence or absence of blue color on the slide was noted (+++=intense color; ++= strong color; +=clearly visible color; ±=barely perceptible color; −=no detectable color). The results of these tests are shown in Table 1 below.

TABLE 1

| Dilution | Hm $H_2O_2$ | Hm CHP | Hb $H_2O_2$ | Hb CHP | HRPO $H_2O_2$ | HRPO CHP |
|---|---|---|---|---|---|---|
| 0 | +++ | +++ | +++ | +++ | +++ | ++ |
| 2 | +++ | +++ | +++ | +++ | +++ | + |
| 4 | +++ | +++ | +++ | +++ | +++ | ± |
| 8 | ++ | ++ | +++ | ++ | +++ | − |
| 16 | ± | + | + | ++ | +++ | − |
| 32 | − | ± | ± | + | ++ | − |
| 64 | − | − | ± | ± | ++ | − |
| 128 | − | − | − | ± | + | − |
| 256 | − | − | − | − | ± | − |
| 512 | − | − | − | − | ± | − |

As indicated by the results of Table 1, the DMSO-based developer was more sensitive than the conventional developer with hemoglobin and hemin and much less sensitive than the conventional developer with horseradish peroxidase. The invention developer thus improves the sensitivity and specificity of the test. Sensitivity can be improved by modifying the developer as needed.

EXAMPLE 2

Hemin degradation tests were carried out using conventional FOBT developer and DMSO-based FOBT developer compositions of the present invention as follows.

Hemin was dissolved in a 1:10 (v/v) mixture of DMSO and water. Two $\mu$l of this solution was spotted onto filter paper and the paper was air dried. Spotted areas were then treated with 5 $\mu$l of one of the following developers: (a) CHP, 5%, in DMSO; (b) t-butyl hydroperoxide, 5%, in DMSO; (c) $H_2O_2$, 5% in water; (d) HEMOCCULT ® developer ($H_2O_2$, 5%, in ethanol/water); (e) DMSO alone; (f) water alone; and (g) 75% ethanol, 25% water. The developer-treated areas were then air dried and 10 $\mu$l of guaiac solution (30 g/1200 ml isopropanol) was applied to each spot followed by air drying. Each spot was then treated with 15 $\mu$l HEMOCCULT ® developer and color change was observed. Visible blue color was noted on each spot except those treated with (c) and (d). These results indicate that organic hydroperoxides in DMSO do not effect adversely the catalytic activity of hemin, whereas conventional FOBT developer does have an adverse effect on hemin activity in FOBT. Similar results were observed using native and denatured hemoglobin instead of hemin.

EXAMPLE 3

Tests were conducted using developer compositions consisting of CHP at 5% in DMSO with various cosolvents. The procedure of Example 1 was used except that the highest clearly detectable dilution of catalyst is noted rather than color intensity. Conventional developer and CHP in other solvents were run for comparison. The results are reported in Table 2 below.

TABLE 2

| Oxidant | Solvent | Highest Detectable Dilution Hm | Hb | HRPO |
|---|---|---|---|---|
| Hydrogen Peroxide | ~75% ethanol | 5 | 5 | 10 |
| CHP | 100% DMSO | 6 | ND | 4 |
| CHP | 75% DMSO 25% Pentane | 5 | ND | 5 |
| CHP | 50% DMSO 50% Pentane | 5 | ND | 6 |
| CHP | 75% DMSO 25% ethyl acetate | 5 | ND | 5 |
| CHP | 75% DMSO 25% Cyclohexane | 5 | ND | 5 |
| CHP | 50% DMSO 50% Cyclohexane | 5 | ND | 5 |
| CHP | Dimethyl Formamide | 7 | 8 | 8 |
| CHP | Acetonitrile | 7 | ND | 9 |
| CHP | 90% DMSO 10% Acetone | 4 | 4 | 3 |
| CHP | 75% DMSO 25% Acetone | 4 | 5 | 3 |
| CHP | 50% DMSO 50% Acetone | 4 | 5 | 5 |
| CHP | 100% EtOH | 4 | 6 | 7 |
| CHP | 100% MeOH | 5 | 8 | 7 |

ND = not determined

The results of Table 2 show that CHP developer with DMSO at >50% show reduced sensitivity of HRPO while retaining sensitivity for hemin. The best results occur using DMSO at 75% and above.

EXAMPLE 4

Tests were carried out to assess the effect of the developer composition on the mobility of hemin spotted on filter paper. This is an indirect measure of the solubility of hemin in the developer.

Whatman filter paper was soaked with 10 $\mu$l of a 1 mg/ml hemin solution in 1 mM aqueous ammonium hydroxide. After drying, a small section of the hemin-treated paper was placed on a HEMOCCULT ® slide. Ten $\mu$l of developer compositions comprising 5% CHP in DMSO/water solvent containing 100%, 95%, 90%, 80%, 75%, 50%, and 25% (v/v) DMSO were placed on the hemin spots and blue color formation was observed.

At DMSO concentrations above about 75% blue color was noted in the entire slide area wetted by the developer. At lower DMSO concentrations color was observed only directly under the hemin-treated filter paper. A similar test with HEMOCCULT ® developer produced no color.

Similar tests using hemoglobin instead of hemin gave similar results.

EXAMPLE 5

This example illustrates the effect of hemin solubility on the readability of FOBT test results.

A normal fecal specimen which tested negative for fecal occult blood with the HEMOCCULT ® FOBT and with an FOBT reagent consisting of 2% guaiac, 1% ABTS, 5% cumene hydroperoxide, and 25 mg/ml 7-chloro-4-(4-diethylamino-1-methylbutylamino) quinoline in 75% DMSO/25% water was spiked with a DMSO solution of hemin sufficient to produce a final hemin concentration of 240 μg/g feces. This level of hemin is equivalent in iron protoporphyrin to 6 mg hemoglobin/g feces. Thin smears of the spiked fecal specimen were added to standard, untreated filter paper and allowed to air dry.

A second FOBT formulation was prepared in tetramethyl urea (2% guaiac, 1% ABTS and 5% cumene hydroperoxide). Fifty microliters of the new FOBT formulation in tetramethyl urea was added to a smear of the spiked fecal specimen on filter paper. No blue color was eluted from the specimen onto the surrounding filter paper. The specimen became somewhat darker in appearance, but it was extremely difficult to decide if a blue color was present because of the dark fecal background.

When a drop of DMSO was added to the spiked fecal specimen which had been treated with the second FOBT formulation, a dark blue color was eluted immediately from the fecal specimen onto the surrounding paper. Similarly, when a drop of aqueous 1 M ethanolamine, pH 7, was added to a spiked fecal specimen which had been treated with the second FOBT formulation, a dark blue color was immediately eluted from the fecal specimen onto the surrounding paper. DMSO is a good heme solvent, and a 1:1 mixture of tetramethyl urea and aqueous 1 M ethanolamine, pH 7, is a good solvent for hemin even through neither tetramethyl urea nor aqueous 1 M ethanolamine alone is a good hemin solvent.

These observations indicate that a good solvent for iron protoporphyrins is extremely important in eluting the color produced in a positive FOBT from a fecal specimen containing iron protoporphyrins. Moreover, the longer the fecal specimen is allowed to dry, the more critical the role of iron protoporphyrin solvent in this regard. In screening programs for colorectal cancer, it is common for fecal smears to be stored for up to 14 days prior to performing the test for fecal occult blood.

EXAMPLE 6

The effect of hemoglobin denaturation on FOBT sensitivity using a DMSO-based developer composition of the invention and HEMOCCULT ® developer was determined as follows.

Hemoglobin was denatured by treatment with (a) hydrochloric acid, (b) enzymes or (c) heat as follows:

(a) Acid

Dilute (0.1 M) hydrochloric acid was added to a solution of hemoglobin in water (5 mg/mol) until the pH of the solution was 1.0. The solution was incubated for 1 hr at 37° C. and the pH adjusted to 7.4 with 0.1 N sodium hydroxide. The resulting material was homogenized to produce a finely dispersed suspension and incubated at 37° C. for 48 hr.

(b) Enzymes

Solid trypsin (1 mg) and chymotrypsin (1 mg) were added to a solution of hemoglobin in water (5 mg/ml) and incubated for 48 hr at 37° C. The resulting mixture was homogenized to produce a smooth suspension.

(c) Heat

A solution of hemoglobin in water (5 mg/ml) was heated to 75° C. for 10 min and incubated at 37° C. for 48 hr. The resulting mixture was homogenized to produce a smooth suspension.

Standard HEMOCCULT ® slides were spotted with 2 μl of an aqueous solution (5 mg/ml) of the denatured hemoglobins or native hemoglobin diluted serially 1:2 with water and allowed to dry. The slides were then treated with developer composition (designated CHP in Table 3 below) consisting of 5% CHP in DMSO/water. Comparison slides were treated with HEMOCCULT ® developer (designated HO in Table 3 below). Color intensities were observed as above. Table 3 reports the results of these tests. (+5=extremely intense color; +1=slight color; —=no color; +/—=barely detectable.)

TABLE 3

| DILUTION | NATIVE | | HEMOGLOBIN TREATMENT | | | | | |
|---|---|---|---|---|---|---|---|---|
| | | | ACID | | ENZYME | | HEAT | |
| | HO | CHP | HO | CHP | HO | CHP | HO | CHP |
| 2 | 5 | 5 | 3 | 3 | 5 | 5 | 5 | 5 |
| 4 | 5 | 5 | 3 | 3 | 4 | 5 | 5 | 5 |
| 8 | 4 | 5 | 2 | 2 | 4 | 4 | 4 | 5 |
| 16 | 4 | 4 | 1 | 2 | 3 | 4 | 3 | 4 |
| 32 | 3 | 4 | +/— | 1 | 2 | 3 | 2 | 3 |
| 64 | 3 | 3 | +/— | 1 | 2 | 3 | 1 | 3 |
| 128 | 2 | 3 | — | 1 | 1 | 2 | 1 | 2 |
| 256 | 2 | 2 | — | 1 | +/— | 2 | +/— | 2 |
| 512 | 1 | 2 | — | 1 | — | 1 | — | 1 |
| 1024 | +/— | 2 | — | +/— | — | 1 | — | 1 |

The data reported in Table 3 indicate that the sensitivity of the FOBT using the DMSO-based developer is not affected by hemoglobin denaturation as much as FOBT using conventional developers. This is particularly significant since such denaturation is likely to occur to hemoglobin in the GI tract.

EXAMPLE 7

This example illustrates the enhanced readability of the multi-chromogen FOBT reagent as regards color intensity and diffusiveness.

The following reagents were prepared:

A. HEMOCCULT® developer (6% hydrogen peroxide in alcohol);

B. 5% cumene hydroperoxide and 2% guaiac in 75% DMSO, 25% water; and

C. 5% cumene hydroperoxide, 2% guaiac, and 25 mg/ml ABTS in 75% DMSO, 25% water containing 100 mg solid sodium sulfite.

Standard HEMOCCULT® slides were smeared with untreated fecal specimens, or with specimens which had been spiked with hemin or hemoglobin (135 or 270 μg hemin/g feces, or with 5.7 mg hemoglobin/g feces). After the smears had dried, the appropriate reagent was added, and the appearance of the test noted at 1 min. The results are reported in Table 4.

TABLE 4

| Fecal Specimen | Hydrogen Peroxide | CHP + Guaiac | ABTS + CHP + Guaiac |
|---|---|---|---|
| 1. Untreated | negative | negative | negative |
| 2. Hemin spiked (135 μg/g) | negative | +1 (hollow center) | +5 (solid circle) |
| 3. Hemin spiked (270 μg/g) | negative | +3 (hollow center) | +10 (solid circle) |
| 4. Homoglobin spiked (2.9 mg/ml) | +1 | +3 | +10 (solid circle) | negative = no color produced.
+1 = very faint blue color.
+10 = extremely intense blue color.
hollow center = blue ring with color at edge of solvent front, and no color in center.
solid circle = even blue color throughout the area covered by the solvent.

EXAMPLE 8

This example shows the relative sensitivity and readability of FOBTs using the multi-chromogen of the invention and reagents containing only ABTS or guaiac.

The following chromogen compositions were used:

A. 2% guaiac and 5% cumene hydroperoxide in 75% DMSO, 25% water.

B. ABTS (10 mg/ml) and 5% cumene hydroperoxide in 75% DMSO, 25% water.

C. 1% guaiac, 5% cumene hydroperoxide, and ABTS (5 mg/ml) in 75% DMSO, 25% water.

A solution of hemin in DMSO (10 mg/ml) was diluted with DMSO in serial fashion 1:2 and the dilutions were spotted (2 μl) onto standard Whatman #1 filter papar. Five μl of reagent was added and color formation noted at 60 sec. The results of these tests are reported in Table 5.

TABLE 5

| Hemin Concentration (mg/ml) | Color Formation | | |
|---|---|---|---|
| | Reagent A | Reagent B | Reagent C |
| 1.00 | + | − | + |
| 0.50 | + | − | + |
| 0.25 | + | − | + |
| 0.13 | + | − | + |
| 0.07 | + | − | + |
| 0.04 | + | − | + |
| 0.02 | + | − | + |
| 0.01 | +/− | − | + |
| 0.005 | +/− | − | +/− |

TABLE 5-continued

| Hemin Concentration (mg/ml) | Color Formation | | |
|---|---|---|---|
| | Reagent A | Reagent B | Reagent C |
| 0.0025 | − | − | +/− |

Color Characteristics:
Reagent A = Blue ring at solvent front, but hollow, colorless center.
Reagent B = No color formed on standard filter paper.
Reagent C = Very intense blue color formed; color evenly distributed throughout the entire solvent area.

EXAMPLE 9

This example shows the chromatographic advantages of the multi-chromogen reagent relative to a single chromogen reagent.

The following reagents were used:

A. Reagent A - 2% guaiac and 5% cumene hydroperoxide in DMSO.

B. Reagent B - Multi-chromogen reagent (2% guaiac, 5% cumene hydroperoxide, and 25 mg/ml ABTS in DMSO over 100 mg solid sodium sulfite).

Two μl of a hemin suspension in water (1 mg/ml) was spotted onto standard Whatman #4 filter paper. After the water had evaporated, varying volumes of Reagent A or Reagent B were added, and the appearance of the blue color noted. Table 6 reports the results of these tests.

TABLE 6

| Reagent Volume | Appearance of Spot | |
|---|---|---|
| | REAGENT A | REAGENT B |
| 5 μl | very slightly disperse | full circle, intense color |
| 10 μl | slightly disperse, hollow center | full circle, intense color |
| 15 μl | disperse circle, hollow center | full circle, intense color |
| 20 μl | very disperse circle, hollow center | intense color, very slightly disperse center |

Color Characteristics:
full circle = Intense blue circle with color evenly distributed throughout the entire area covered by the solvent.
very slightly disperse circle = Blue circle, but small, faint, colorless area at center of circle.
slightly disperse = Blue circle, approximately 20% of central area colorless.
disperse circle = Blue ring, approximately 50% of the central area colorless.
very disperse circle = blue ring with >80% of the central area colorless; color is primarily localized at the solvent front.

EXAMPLE 10

This example illustrates enhanced color intensity and uniformity obtained using the multi-chromogen reagent.

The following reagents were used:

A. 2% guaiac and 5% cumene hydroperoxide in DMSO.

B. 2% guaiac and 5% cumene hydroperoxide and ABTS (25 mg/ml) in DMSO containing 100 mg solid sodium sulfite.

Two μl hemin solution (0.05 mg/ml) in DMSO was spotted onto untreated Whatman #1 filter paper. Ten μl reagent A or B was added and the appearance noted in 1–3 min. Each test was run in triplicate. Table 7 reports the results of the tests.

TABLE 7

| | REAGENT A | | REAGENT B | |
|---|---|---|---|---|
| | Intensity | Appearance | Intensity | Appearance |
| 1. | +3 | Blue ring with | +10 | Solid blue circle |

TABLE 7-continued

| | REAGENT A | | REAGENT B | |
|---|---|---|---|---|
| | Intensity | Appearance | Intensity | Appearance |
| | | hollow center | | intensely blue |
| 2. | +3 | Blue ring with hollow center | +10 | Solid blue circle intensely blue |
| 3. | +3 | Blue ring with hollow center | +10 | Solid blue circle intensely blue |

Color Characteristics:
Blue ring with hollow center = Blue color at edge of solvent front, but no color in center.
Solid blue circle = Even, blue color throughout the area covered by the solvent.
+1 = very faint blue
+10 = extremely intense blue

EXAMPLE 11

This example provides a comparison of color intensity, stability and chromatography in tests using the HEMOCCULT® reagents and the multiple-chromogen of the invention, with hemin as catalyst.

The following reagents were used:
A. HEMOCCULT® developer (6% hydrogen peroxide in alcohol).
B. Multi-chromogen reagent (1% guaiac, 5% cumene hydroperoxide, and ABTS (25 mg/ml) in DMSO).

Two μl of a suspension of hemin in water (0.25 mg/ml) was added to standard HEMOCCULT® slides, and the spots allowed to dry. Five μl of each reagent was added to the spots, and color formation noted at 30 sec, 60 sec, 3 min, and 5 min. Table 8 reports the results of these tests.

TABLE 8

| | COLOR FORMATION | | | |
|---|---|---|---|---|
| | HEMOCCULT DEVELOPER | | MULTIPLE CHROMOGEN REAGENT | |
| Time | Intensity | Appearance | Intensity | Appearance |
| 30 sec | +2 | diffuse, uneven color | +8 | intense full circle color |
| 60 sec | +1 | diffuse, uneven color | +10 | intense full circle color |
| 3 min | neg | no color | +7 | intense full circle color |
| 5 min | neg | no color | +7 | intense full circle color |

Color Characteristics:
Reagent A = Weak, diffuse color with streaking.
Reagent B = Extremely intense blue color. Color is evenly distributed throughout the area covered by the solvent.

EXAMPLE 12

This example reports the sensitivity of complete multiple-chromogen FOBT to plant peroxidases relative to other reagents.

The following reagents were used:
A. Horseradish Peroxidase, 1,000 Units/ml.
B. HEMOCCULT® developer (6% hydrogen peroxide in alcohol).
C. 5% cumene hydroperoxide in DMSO.
D. 5% cumene hydroperoxide in DMSO containing 2% guaiac.
E. 5% cumene hydroperoxide in DMSO containing 2% guaiac and ABTS (25 mg/ml) stored over solid sodium sulfite.

The horseradish peroxidase was diluted in serial fashion with 1:2 with distilled water. Two μl of the dilutions were spotted in quaruplicate on standard HEMOCCULT® slides. The spots were allowed to dry, and 5 μl of the appropriate reagent added. Color was determined at 60 sec. The results of these tests are reported in Table 9.

TABLE 9

| | COLOR FORMATION | | | |
|---|---|---|---|---|
| (Units/ml) | RE-AGENT B | RE-AGENT C | RE-AGENT D | RE-AGENT E |
| 2.00 | + | + | + | + |
| 1.00 | + | + | + | + |
| 0.50 | + | + | + | + |
| 0.25 | + | + | + | − |
| 0.13 | + | +/− | + | − |
| 0.07 | + | − | + | − |
| 0.04 | + | − | +/− | − |
| 0.02 | + | − | +/− | − |
| 0.01 | + | − | − | − |
| 0.005 | + | − | − | − |
| 0.0025 | +/− | − | − | − |
| 0.0013 | +/− | − | − | − |
| 0.0007 | +/− | − | − | − |
| 0.0004 | +/− | − | − | − |
| 0.0002 | − | − | − | − |

EXAMPLE 13

This example shows the effect of sulfite on the multiple-chromogen reagent stability.

Multiple component reagent containing 5% cumene hydroperoxide and 10.1 mg/ml ABTS in DMSO was made by adding guaiac or solid sodium sulfite as indicated in Table 10 below. Sodium sulfite was present either as excess solid, or as a saturated solution in DMSO from which all crystals were removed by filtration.

Procedure

Each reagent was tested for its ability to detect 2 μl of a hemin solution (1 mg/ml) in DMSO on standard Whatman filter paper #1. Ten μl of reagent were used. The results are reported in Table 10.

TABLE 10

| REAGENT COMPOSITION | | | COLOR FORMATION | |
|---|---|---|---|---|
| ABTS (%) | Guaiac (%) | Sulfite Added | Day One | Day 120 |
| 1.0 | 2.0 | none | + | − |
| 1.0 | 2.0 | saturated (no excess solid) | + | − |
| 1.0 | 2.0 | excess solid | + | + |
| 1.0 | none | none | +/− | − |
| 1.0 | none | excess solid | +/− | − |

EXAMPLE 14

This example illustrates other iron protoporphyrin solvents comprising a mixture of ethanolamine, 2-(diethylamino)ethylamine, or diethanolamine with various organic solvents which, by themselves are not good iron protoporphyrin solvents.

Twenty-five mg crystalline hemin was added to a test tube. One ml of amine-containing solvent was added to the tube and the tube was vortexed. Amines used were in 1 M aqueous solutions at pH 7. Amines were mixed with co-solvents at a volume ratio of 1:1. the solubility of the hemin in the solvent was evaluated using the following scale. O=non-miscible, 1=slight solubitlity, 2 to 4=intermediate solubility, and 5=complete solubility. Solvent systems having readings of 4 or 5 were considered acceptable FOBT solvents. Table 11 below reports the results of these tests.

TABLE 11

| Co-solvent | Hemin Solubility | | | |
|---|---|---|---|---|
| | None | Ethanol-amine | 2-(diethyl-amino)ethyl-amine | Di-ethanol mine |
| None | x | 1 | 2 | 1 |
| Methyl ethyl ketone | 1 | 5 | 5 | 5 |
| Acetonitrile | 0 | 0 | 5 | 5 |
| Tetramethylene sulfone | 1 | 5 | 5 | 5 |
| Butyrolactone | 2 | 5 | 5 | 4 |
| Tetrahydrofurfuryl alcohol | 1 | 5 | 5 | 5 |
| 2-Methoxy ethanol | 1 | 5 | 5 | 5 |
| Methanol | 1 | 3 | 5 | 2 |
| Tetramethyl urea | 2 | 5 | x | x |
| Glycerol/$H_2O$ 1:1 v/v | 0 | 4 | x | x |

Modifications as the above modes for carrying out the invention that are obvious to those of skill in the fields of medicine, biochemistry and, in particular FOBT, are intended to be within the scope of the following claims.

I claim:

1. In a method for detecting the presence of a peroxidatively active substance in a sample suspected of containing such a substance wherein the sample is contacted with a chromogen and a hydroperoxide, the improvement wherein the chromogen is a mixture of guaiac and 2,2'-azino-di-(3-ethylbenzyl) thiazoline sulfonic acid (ABTS) in a weight ratio of guaiac to ABTS in the range of 1:5 to 5:1.

2. The method of claim 1 wherein the sample is a fecal specimen on a solid test matrix.

* * * * *